(12) United States Patent
Ichikawa et al.

(10) Patent No.: US 6,700,026 B1
(45) Date of Patent: Mar. 2, 2004

(54) METHOD FOR PREPARING DIFLUOROMETHANE

(75) Inventors: Masaru Ichikawa, Sapporo (JP); Ryuichirou Ohnishi, Sapporo (JP)

(73) Assignee: Daikin Industries Ltd., Osaka (JP)

( * ) Notice: Subject to any disclaimer, the term of this patent is extended or adjusted under 35 U.S.C. 154(b) by 0 days.

(21) Appl. No.: 08/751,557

(22) PCT Filed: Nov. 9, 1993

(86) PCT No.: PCT/JP93/01622
§ 371 (c)(1), (2), (4) Date: Jun. 8, 1995

(87) PCT Pub. No.: WO94/11328
PCT Pub. Date: May 26, 1994

Related U.S. Application Data

(63) Continuation of application No. 08/433,458, filed as application No. PCT/JP93/01622 on Nov. 9, 1993, now abandoned.

(30) Foreign Application Priority Data

Nov. 11, 1992 (JP) .............................................. 4-326103

(51) Int. Cl.⁷ ................................................ C07C 17/10
(52) U.S. Cl. ...................................................... 570/176
(58) Field of Search .......................................... 570/176

(56) References Cited

FOREIGN PATENT DOCUMENTS

| EP | 0508660 | * | 10/1992 |
| JP | 242536 | * | 9/1989 |
| JP | 3-99026 A | | 4/1991 |

* cited by examiner

*Primary Examiner*—Samuel Barts
*Assistant Examiner*—Elvis O. Price
(74) *Attorney, Agent, or Firm*—Birch, Stewart, Kolasch & Birch, LLP

(57) ABSTRACT

A method for preparing difluoromethane ($CF_2H_2$, HFC-32) by the use of reaction of dichlorodifluoromethane ($CF_2Cl_2$, CFC-12) and/or monochlorodifluoromethane ($CF_2ClH$, HCFC-22) with hydrogen in the presence of a palladium-based catalyst can give difluoromethane at a high conversion and a high selectivity.

9 Claims, No Drawings

METHOD FOR PREPARING DIFLUOROMETHANE

This application is a continuation, divisional, continuation-in-part, of application Ser. No. 08/433,458 filed on Jun. 8, 1995 now abandoned which is a 371 of Ser. No. PCT/JP93/01622 filed Nov. 9, 1993.

BACKGROUND OF THE INVENTION

1. Field of the Invention

The present invention relates to a method for preparing difluoromethane ($CF_2H_2$) which is used as a refrigerant and the like and is a substitute for a fluorinated gas.

2. Related Art

Methods for preparing $CF_2H_2$ (hereinafter referred to as HFC-32 include a process of reducing $CF_2Cl_2$ (hereinafter referred to as CFC-12), as described in UK Patent No. 732269; and a process of fluorinating $CH_2Cl_2$ (dichloromethane), as described in Japanese Patent Kokoku Publication No. 3004/1967 (corresponding to U.S. Pat. No. 226447), and Japanese Patent Kokai Publication Nos. 225131/1984, 231029/1984, and 231030/1984.

The former process conduct the reduction with hydrogen at a temperature of 400 to 1,000° C. in the presence of a Pt, Pt alloy, Cu, Ag or Co catalyst. In the latter process, the catalyst used includes dichromium trioxide, chromium fluoride, aluminum fluoride and a mixture thereof.

HFC-32 draws attention as a substitute for CFC-12 ($CF_2Cl_2$, dichlorodifluoromethane) and HCFC-22 ($CF_2ClH$, monochlorodifluoromethane). Accordingly, if HFC-32 can be prepared from the CFC-12 or HCFC-22 raw material, an existing apparatus can be effectively used. In this case, a reaction for reducing the raw material is necessary.

However, a hitherto known reduction method has a high reaction temperature of at least 400° C. and results in excess reduction in the case that each of HCFC-22 and CFC-12 is used as the raw material, whereby a large amount of evolved methane is produced so that the selectivity of HFC-32 is low. For example, if the reaction is conducted at the temperature of 720° C., the conversion of CFC-12 is 66% and a selectivity of HCFC-32 is only 13.2% (cf. UK Patent No. 732269).

SUMMARY OF THE INVENTION

An object of the present invention is to provide a method for preparing HFC-32 from a CFC-12 or HCFC-22 raw material so as to provide both a high conversion and a high HFC-32 selectivity.

The present invention provides a method for preparing difluoromethane ($CF_2H_2$, HFC-32) which includes reacting dichlorodifluoromethane ($CF_2Cl_2$, CFC-12) and/or monochlorodifluoromethane ($CF_2ClH$, HCFC-22) with hydrogen in the presence of a palladium-based catalyst.

DETAILED DESCRIPTION OF THE INVENTION

The palladium-based catalyst is preferably a palladium (Pd) catalyst; or a catalyst in which at least one metal selected from the group consisting of vanadium (V), zirconium (Zr), calcium (Ca), magnesium (Mg), niobium (Nb) and tantalum (Ta) is added to palladium.

The above reaction (hydrogenation reaction) in the present invention is preferably conducted at a temperature of 120 to 400° C.

The palladium-based catalyst used in the present invention comprises a carrier and an active metal component. The active metal component is preferably a palladium metal or a combination of a palladium metal with at least one additional metal selected from the group consisting of vanadium, zirconium, calcium, magnesium, niobium and tantalum. An amount of palladium supported in the catalyst is preferably from 0.5 to 5% by weight. A molar ratio of the additional metal to Pd is usually from 0.01 to 4, preferably from 0.1 to 2. Since the large molar ratio does not give a significant effect on a selectivity and gives a decrease of reaction conversion, the molar ratio is preferably at most 4. A size of the catalyst is not limited and is usually from 1 to 6 mm. A powdery catalyst may be used.

The additional metal may be in the form of a salt. A nitrate salt, a metal oxide salt, an oxide and a chloride salt can be used. The carrier may be one usually used in conventional catalysts, such as active carbon and alumina. Since HF may evolve in the method of the present invention, it is undesirable to use a catalyst which has no resistance to HF.

One example of procedure for supporting the additional metal on the carrier is explained hereinafter. However, the present invention is not limited to this example. A salt of an additional metal is dissolved in water. Formalin and a powdery catalyst having Pd supported on active carbon are added to water and aged. The additional metal is dissolved in such amount that the desired molar ratio of the additional metal to palladium is achieved. Then, after water is evaporated, the catalyst is dried in air. Before the method of the present invention, the catalyst may be pretreated at 300–500° C. for 0.1–10 hours in a hydrogen stream.

In the reaction of the present invention, a molar ratio of hydrogen to CFC-12 or HCFC-22 is usually from 1 to 10. When the molar ratio is from 1 to 10, the selectivity is not adversely affected and the reaction seldom gives an excessively hydrogenated paraffin compound. The W/F (W: weight of catalyst (g), F: total flow rate of raw material and hydrogen (ml/sec at STP)) corresponding to a contact time is preferably from 0.01 to 10. When the W/F is up to about 10, the W/F gives an effect only on the reaction conversion with a slight change of the selectivity.

The method of the present invention is usually conducted in a gas phase. A reaction temperature is usually from 120 to 400° C., preferably from 200 to 300° C. A reaction pressure is usually from 1 to 10 atm, preferably from 1 to 5 atm. According to the present invention, when the reaction temperature is from 200 to 300° C., the reaction gives the result that a conversion from CFC-12 is 91% and a selectivity to HFC-32 is 81%.

In the reaction of the present invention, a raw material is either CFC-12 or HCFC-22; or combination thereof.

According to the method of the present invention, the reaction of CFC-12 and/or HCFC-22 with hydrogen in the presence of the palladium-based catalyst at the temperature of at most 400° C. gives a higher conversion and a higher HFC-32 selectivity.

PREFERRED EMBODIMENT OF THE INVENTION

The present invention will be illustrated by the following Examples.

EXAMPLE 1

An additional metal (namely, Zr) was supported on a catalyst material in which 5% by weight of Pd is supported on active carbon (a commercially available catalyst manufactured by N. E. CHEMICAL CATALYST) to prepare a catalyst. A molar ratio of Zr/Pd in the resultant catalyst was 0.5. 0.083 g of zirconyl chloride was dissolved in 30 ml of water. 2 g of the powdery catalyst material in which Pd is supported on active carbon and 0.2 g of formalin were added to water and aged at 50° C. for 2–3 hours. Then, water was removed by the use of a rotary evaporator and a solid material was dried at 100° C. for 12 hours in air. Before a hydrogenation reaction of CFC-12, the catalyst was treated at 400° C. for 2 hours so as to conduct a pretreatment of the catalyst.

A SUS-314 reaction tube having an internal diameter of 10 mm was filled with 1 g of catalyst. While keeping the reaction tube at a temperature of 250° C., a combination of 10 Nml/min of CFC-12 and 30 Nml/min of $H_2$ was passed through the reaction tube.

A conversion of CFC-12 was 91%. A selectivity was 81% of HFC-32, 14% of methane, 1% of ethane and 3% of HCFC-22.

EXAMPLE 2

The reaction was conducted in the same manner as in Example 1, except that the reaction temperature was 200° C. A conversion of CFC-12 was 75%. A selectivity was 82% of HFC-32, 13% of methane, 1% of ethane and 4% of HCFC-22.

EXAMPLE 3

The reaction was conducted in the same manner as in Example 1, except that the flow rates of CFC-12 and $H_2$ were 4 Nml/min and 9 Nml/min, respectively. A conversion of CFC-12 was 89%. A selectivity was 70% of HFC-32, 21% of methane, 5% of ethane, 2% of HCFC-22 and 2% of HFC-23 ($CF_3H$).

EXAMPLE 4

The reaction was conducted in the same manner as in Example 1, except that the molar ratio of Zr/Pd was 0.2. A conversion of CFC-12 was 89%. A selectivity was 82% of HFC-32, 12% of methane, 2% of ethane and 4% of HCFC-22.

EXAMPLE 5

The reaction was conducted in the same manner as in Example 1, except that the molar ratio of Zr/Pd was 1. A conversion of CFC-12 was 62%. A selectivity was 67% of HFC-32, 20% of methane, 7% of ethane and 6% of HCFC-22.

EXAMPLE 6

The reaction was conducted in the same manner as in Example 1, except that the molar ratio of Zr/Pd was 1.5. A conversion of CFC-12 was 82%. A selectivity was 76% of HFC-32, 13% of methane, 6% of ethane, 4% of HCFC-22 and 1% of HFC-23.

EXAMPLE 7

The reaction was conducted in the same manner as in Example 1, except that ammonium metavanadate was used as the supported metal salt and the molar ratio of V/Pd was 0.2. A conversion of CFC-12 was 74%. A selectivity was 81% of HFC-32, 15% of methane and 4% of HCFC-22.

EXAMPLE 8

The reaction was conducted in the same manner as in Example 1, except that magnesium chloride was used as the supported metal salt and the molar ratio of Mg/Pd was 1. A conversion of CFC-12 was 40% and a selectivity of HFC-32 was 81%.

EXAMPLE 9

The reaction was conducted in the same manner as in Example 1, except that calcium chloride was used as the supported metal salt and the molar ratio of Ca/Pd was 1. A conversion of CFC-12 was 52% and a selectivity of HFC-32 was 78%.

EXAMPLE 10

The reaction was conducted in the same manner as in Example 1, except that niobium chloride oxide was used as the supported metal salt and the molar ratio of Nb/Pd was 1. A conversion of CFC-12 was 52% and a selectivity of HFC-32 was 78%.

EXAMPLE 11

The reaction was conducted in the same manner as in Example 1, except that tantalum chloride was used as the supported metal salt and the molar ratio of Ta/Pd was 0.5. A conversion of CFC-12 was 46% and a selectivity of HFC-32 was 82%.

EXAMPLE 12

The reaction was conducted in the same manner as in Example 1, except that a metal other than Pd was not supported in the catalyst. A conversion of CFC-12 was 64%. A selectivity was 74% of HFC-32, 19% of methane, 1% of ethane and 6% of HCFC-22.

EXAMPLE 13

The reaction was conducted in the same manner as in Example 7, except that HCFC-22 was used instead of CFC-12, the flow rates of HCFC-22 and $H_2$ were 10 Nml/min and 20 Nml/min respectively, the reaction temperature was 380° C., and the molar ratio of V/Pd was 1. A conversion of HCFC-22 was 62%. A selectivity was 76% of HFC-32, 22% of methane, 1% of ethane and 1% of HCFC-23.

EXAMPLE 14

The reaction was conducted in the same manner as in Example 13, except that the molar ratio of V/Pd was 0.5. A conversion of HCFC-22 was 63%. A selectivity was 73% of HFC-32, 24% of methane and 3% of HFC-23.

EXAMPLE 15

The reaction was conducted in the same manner as in Example 13, except that a metal other than Pd was not supported in the catalyst. A conversion of HCFC-22 was 43%. A selectivity was 72% of HFC-32, 24% of methane and 4% of HFC-23.

What is claimed is:

1. A method for preparing difluoromethane comprising:
    reacting dichlorodifluoromethane and/or monochlorodifluoromethane with hydrogen in the presence of a palladium-based catalyst,
    wherein the palladium-based catalyst is a catalyst in which at least one additional metal selected from the group consisting of vanadium, zirconium, calcium, magnesium, niobium and tantalum is added to palladium.

2. The method according to claim 1, wherein the reaction is conducted at a temperature of 120 to 400° C.

3. The method according to claim 1, wherein the molar ratio of the additional metal to the palladium is 0.01 to 4.

4. The method according to claim 1, wherein the molar ratio of the additional metal to the palladium is 0.1 to 2.

5. The method according to claim 1, wherein the molar ratio of hydrogen to the dichlorodifluoromethane and/or monochlorodifluoromethane is from 1 to 10.

6. The method according to claim 1, wherein the reaction is conducted at a temperature of 200 to 300° C.

7. The method according to claim 2, wherein the molar ratio of the additional metal to the palladium is 0.01 to 4, and wherein the molar ratio of hydrogen to the dichlorodifluoromethane and/or monochlorodifluoromethane is from 1 to 10.

8. The method for preparing difluoromethane according to claim 1, wherin method is conducted in a gas phase.

9. The method for preparing difluoromethane according to claim 1, wherein the said additional metal is vanadium, calcium or magnesium.

* * * * *